United States Patent
Tomisaka et al.

[11] Patent Number: 5,132,057
[45] Date of Patent: Jul. 21, 1992

[54] METHOD OF MAKING AN OPTICAL FIBER PROBE

[75] Inventors: Dennis M. Tomisaka, Dublin; John C. Toomey, West Worthington, both of Ohio

[73] Assignee: Medex, Inc., Hilliard, Ohio

[21] Appl. No.: 688,869

[22] Filed: Apr. 22, 1991

Related U.S. Application Data

[62] Division of Ser. No. 419,692, Oct. 11, 1989, Pat. No. 5,056,520.

[51] Int. Cl.⁵ .................. B05D 7/22; B29C 65/54; B29D 11/00
[52] U.S. Cl. .................. 264/1.4; 156/305; 264/1.5; 264/262; 264/263; 427/163; 427/238
[58] Field of Search .................. 385/12, 78, 80; 128/634, 636; 427/54.1, 163, 238; 156/87, 275.5, 275.7, 278, 294, 305; 264/1.4, 1.5, 262, 1.7, 22, 516, 263; 422/82.06, 82.07

[56] References Cited

U.S. PATENT DOCUMENTS

| Re. 31,879 | 5/1985 | Lubbers et al. | 128/636 |
|---|---|---|---|
| 3,301,648 | 1/1967 | Sheldon | 264/1.5 |
| 4,061,522 | 12/1977 | Bauerkemper | 264/263 |
| 4,200,110 | 4/1980 | Peterson et al. | 128/636 |
| 4,301,192 | 11/1981 | Plichta et al. | 427/238 |
| 4,378,954 | 4/1983 | Baker | 156/294 |
| 4,389,428 | 6/1983 | McDuffee et al. | 264/1.5 |
| 4,452,904 | 6/1984 | Haagensen | 436/545 |
| 4,682,895 | 7/1987 | Costello | 128/634 |
| 4,824,789 | 4/1989 | Yafuso et al. | 128/634 |
| 4,842,783 | 6/1989 | Blaylock | 264/1.5 |
| 4,854,321 | 8/1989 | Boiarski | 128/634 |
| 4,919,891 | 4/1990 | Yafuso et al. | 385/12 |
| 4,952,655 | 8/1990 | Seelmann | 526/318.4 |
| 4,954,318 | 9/1990 | Yafuso et al. | 128/634 |
| 5,037,615 | 8/1991 | Kane | 128/634 |
| 5,061,336 | 10/1991 | Soane | 264/1.4 |
| 5,063,178 | 11/1991 | Toomey | 128/634 |

Primary Examiner—Michael W. Ball
Assistant Examiner—Steven D. Maki
Attorney, Agent, or Firm—Wood, Herron & Evans

[57] ABSTRACT

In a blood gas sensing probe, a cylindrical sleeve contains an optical fiber. The end of the optical fiber is withdrawn into the sleeve thereby creating a receptacle at the end of the sleeve. A sensitive dye, HOPSA for example, is encapsulated in a gel and deposited in the receptacle to form the probe. In making the probe, the end of the optical fiber is in the same plane as the end of the sleeve in which it is placed. The dye and gel contact the combined ends of optical fiber and sleeve. The fiber is withdrawn into the sleeve thereby creating a vacuum which is filled by the dye and gel.

5 Claims, 2 Drawing Sheets

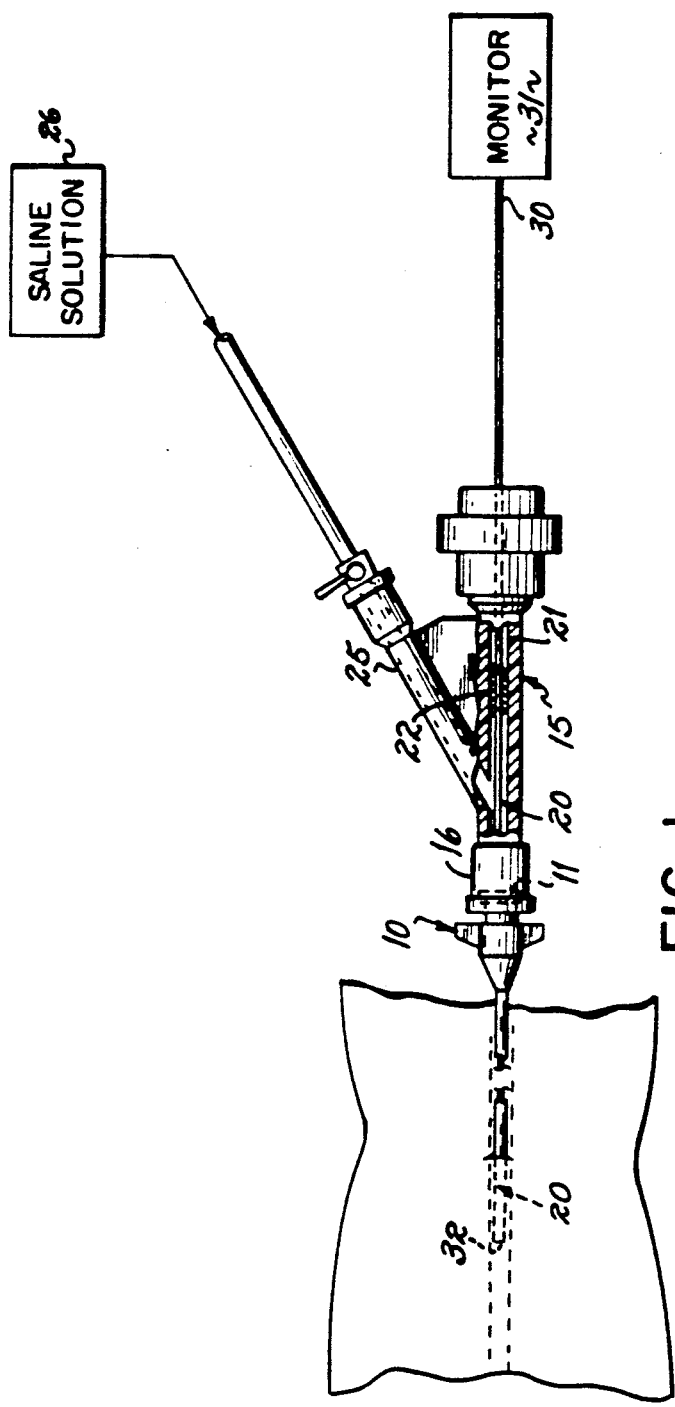
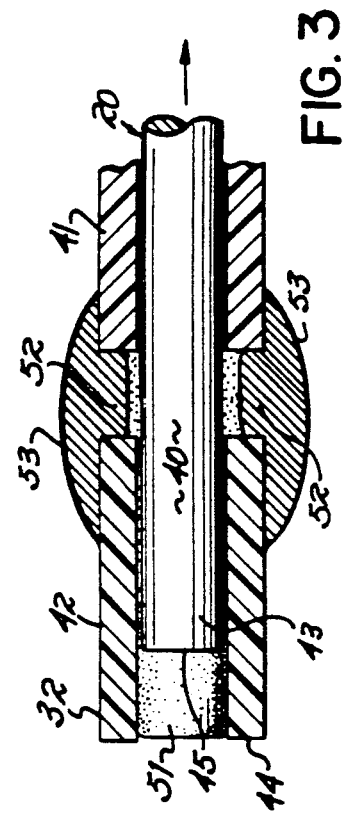
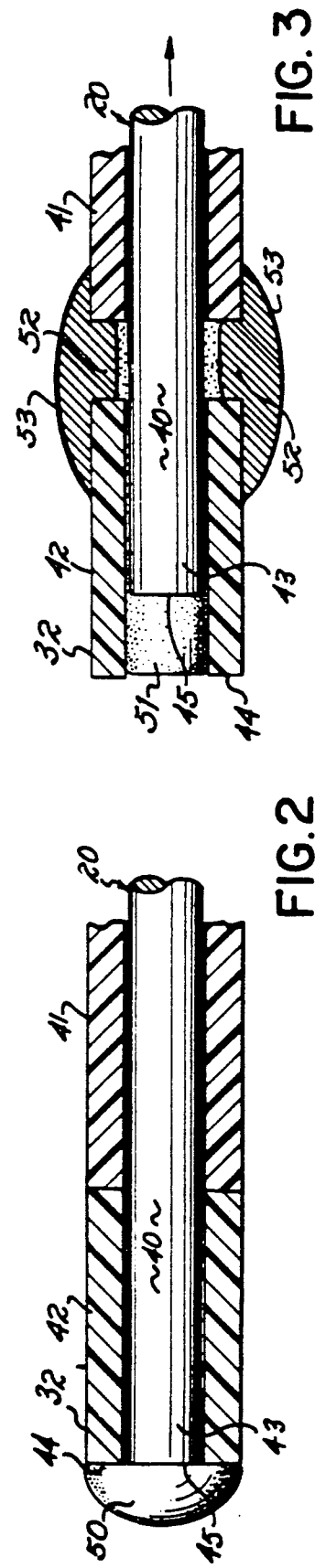
FIG. 1
FIG. 2
FIG. 3

METHOD OF MAKING AN OPTICAL FIBER PROBE

This is a division of application Ser. No. 07/419,692, filed Oct. 11, 1989 now U.S. Pat. No. 5,056,520.

BACKGROUND OF THE DISCLOSURE

This invention relates to a probe for sensing pH of the blood although the probe constructed in accordance with the principles of the present invention could be used for sensing other blood gases or electrolytes.

The concept of mounting a blood gas sensitive dye on the end of an optical fiber, exciting the dye with light passing through the optical fiber and measuring the partial pressure of the blood gas by measuring some aspect of the excited fluorescent dye is known. See, for example, U.S. Pat. No. Re. 31,879, issued May 7, 1985, Lubbers et al, and U.S. Pat. No. 4,200,110, issued Apr. 29, 1980, Peterson et al. This concept is of great importance to the medical profession, for its permits the real time monitoring of a patient's condition during medical/surgical procedures.

In spite of the very considerable need for a probe tiny enough to be insertable into the blood vessels of a patient, no probe has enjoyed any measurable commercial success.

An objective of the present invention has been to provide an improved probe and a method of making it.

Another more specific objective of the present invention has been to provide a method, and an article produced from the method, for placing a sensor/gel on the end of a tiny optical fiber. The optical fiber in the illustrated form of the invention is 0.009" in diameter.

The objectives of the invention are obtained by providing a sleeve around the optical fiber. Initially, the ends of the sleeve and optical fiber coincide, that is to say, they lie in the same plane. The fiber/sleeve combination is placed into a drop of sensor matrix, i.e., a mixture containing a fluoroscent indicator, the monomer, and polymerization initiator, which is curable to provide a sensor gel. The fiber is pulled back with respect to the sleeve thereby creating a pocket and a vacuum in the pocket which is immediately filled by the flow of the sensor matrix into the thus formed pocket. Thus, it is that a very tiny volume (a cylinder approximately 0.009" long and 0.010" diameter) of the sensor matrix is mounted on the end of an optical fiber without the possibility of oxygen occurring at the interface between the end of the fiber and the sensor matrix. The sensor matrix is then cured to provide a stable sensor gel on the end of the probe.

Curing the sensor matrix using conventional heating means to provide the desired sensor gel requires heating the sensor matrix in an oven for three to five hours. In accordance with one aspect of the present invention, the sensor matrix is cured by subjecting it to ultraviolet light for a period of about twenty seconds. The particular combination of components in the sensor which permits this twenty-second ultraviolet light cure includes a derivative of HOPSA (HOPSA is an acronym for 8-Hydroxy-1,3,6-pyrenetrisulfonic acid trisodium salt), acrylamide monomers, and an azo-polymerization initiator.

It was necessary to prepare a derivative of the HOPSA indicator that contained an alkene function which would copolymerize with the acrylamide monomers of which the hydrogel portion of the sensor gel is made. The hydrogel is the support material in which the indicator is copolymerized and held while still allowing molecular contact with the analyte to be measured. Through numerous tests, a HOPSA derivative was found which appeared to be held very strongly within the polyacrylamide hydrogel upon curing of the sensor matrix. That derivative, di-substituted HOPSA (2-propenyl)sulfonamido, which for ease of reference will be referred to hereinafter as "di-substituted HOPSA", has the following structural formula:

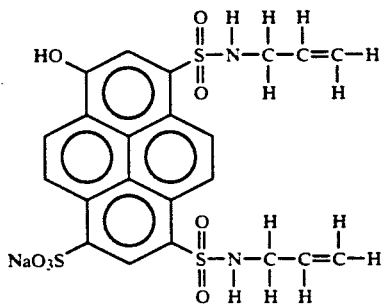

Another aspect of the present invention involves creating and maintaining an oxygen-free atmosphere throughout the curing (polymerization) process in order to eliminate the presence of oxygen which competes against the acrylamide monomers for the initiator. This not only slows the cure of the polyacrylamide, it may also detrimentally affect the sensitivity of the sensor gel.

Another feature of the present invention resides in the mounting of a fiber in a Y-connector which, in turn, can be connected to a catheter through which the optical fiber and sleeve, with the sensor on its end, can be inserted into the blood vessel of a patient.

BRIEF DESCRIPTION OF THE INVENTION

The several objectives and features of the present invention will become more readily apparent from the following detailed description taken in conjunction with the accompanying drawings in which:

FIG. 1 is a diagrammatic view of the sensor as applied to a patient's arm;

FIGS. 2 and 3 are diagrammatic views of the sensor and method of making it; and

DETAILED DESCRIPTION OF THE INVENTION

Figure 4:
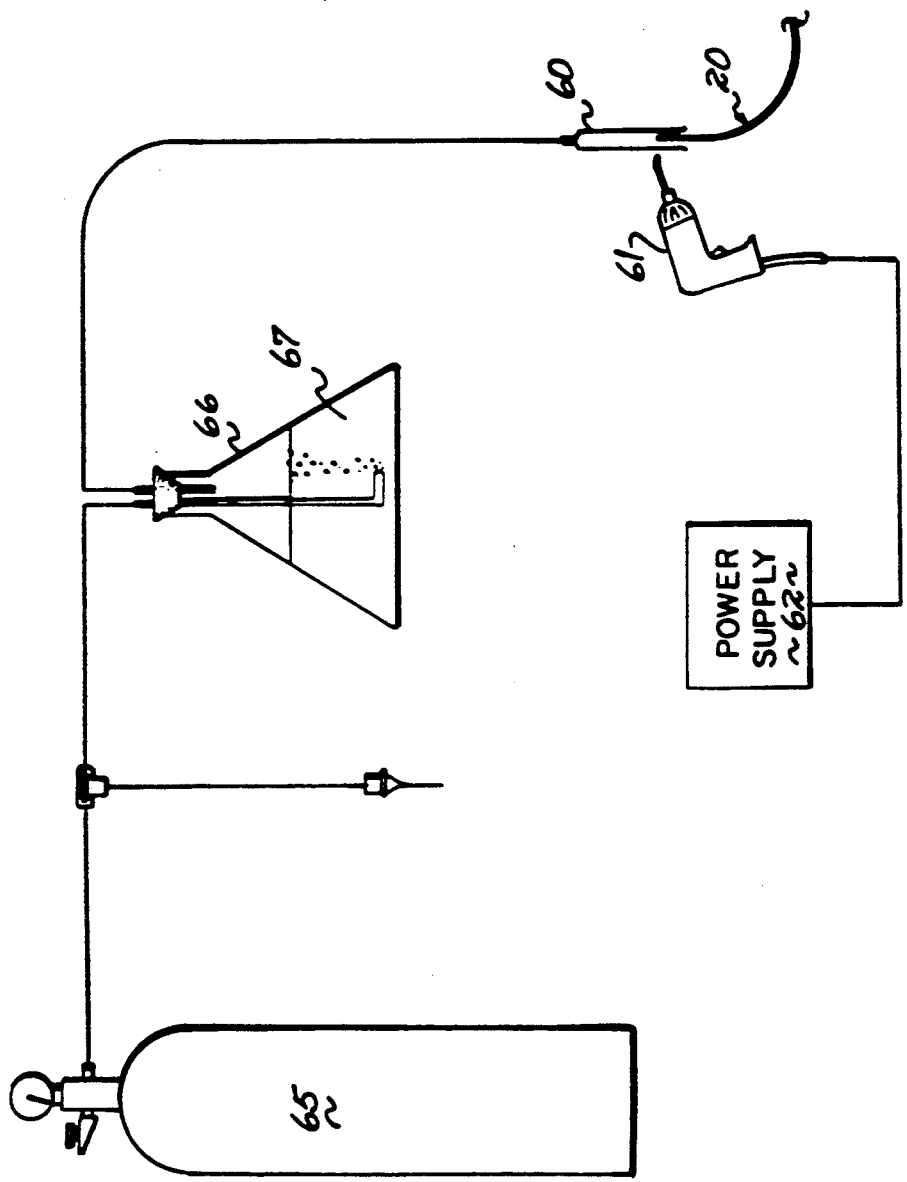
FIG. 4 is a diagrammatic view of the method of curing the sensor gel after it has been drawn into the sensor tip.

Referring to FIG. 1, the sensor is shown as applied to a blood vessel in a patient's arm. A catheter 10 is inserted in the patient's arm. The catheter has a male Luer connection 11 on one end. A Y connector 15 has a female Luer connection 16 on one end adapted to receive the male connection 11. An elongated sensor 20 passes through the main branch 21 of the Y connector and is sealed there by a cement such as cyanoacrylate, indicated at 22. The sensor 20 passes through the catheter 10 which is connected to the Y-connector 15 by the Luer connection 11, 16.

The Y connector 15 has a branch 25 which is connected to a saline solution 26 which is slowly passed through the catheter to help maintain the sensor free from blood clotting. The sensor 20 has a section 30 upstream from the plastic seal 22 that is connected to a monitor 31. The monitor 31 contains the light source that is directed through the optical fiber to a sensor gel in the sensor tip 32 to excite the fluorescent HOPSA-derivative indicator held in the gel. The intensity of excitation is measured by the monitor and that provides a continuous measure of the pH in the patient's blood. See the Boiarski U.S. patent application Ser. No. 07/282,961, now U.S. Pat. No. 4,854,321 filed Dec. 2, 1988, whose disclosure is incorporated herein by reference and forms a part of the application. This application discloses a method of excitation and measuring the level of intensity.

FIGS. 2 and 3 disclose the details of the sensor tip and its method of applying the sensor matrix to it. An optical fiber 40 having a length as desired for the particular application is clad in a jacket 41. The optical fiber is preferably 0.009" in diameter. The fiber is preferably a 200/225μ silica optic fiber. A sleeve consisting of fused silica capillary tubing 42 is slidably mounted on a free end 43 of the optic fiber 40. The sleeve 42 has an I.D. of 0.010", thereby providing a snug, substantially air-free, fit between the fiber 40 and the sleeve 42. The sleeve 42 has an end surface 44 and the optic fiber 40 has an end surface 45, those end surfaces being substantially coextensive with each other, that is, lying in the same plane, at the beginning of the operation to apply the dye to the end 45 of the optic fiber.

The sensor matrix liquid mixture containing the HOPSA-derivative indicator, monomers and polymerization initiator is formed as described hereafter. A drop 50 of that sensor matrix is applied across the surfaces 44, 45 of the sleeve 42 and optic fiber 40, respectively. The end 43 of the optic fiber is then slid inwardly with respect to the sleeve a distance of about 0.009" create a cavity or receptacle 51 whose diameter is 0.010" and whose length is 0.009". The creation of that receptacle 51 causes the creation of a vacuum which drives the sensor matrix into the receptacle. Capillary action along the cylindrical space between the sleeve 42 and fiber 40 causes the sensor matrix to flow by capillary action into that space, thereby driving out the air. The air is permitted to escape through a gap 52 between the sleeve 42 and the cladding 41 around the fiber. That space 52 is thereafter sealed by applying the cyanoacrylate to it as indicated at 53.

The sensor matrix must be cured to provide a stable sensor gel. Conventionally, sensor matrices of the type employed herein are cured by baking in an oven over a period of three to five hours. In accordance with the present invention, the matrix is cured by subjecting it to ultraviolet light for a period of about twenty seconds as shown in FIG. 4. To this end, a curing chamber 60 is formed by a Pasteur pipet. A light gun 61 and power supply 62 is capable of delivering a high intensity ultraviolet light at an intensity of 50 mW/CM$^2$ onto the sensor in curing chamber 60. The curing is performed in an oxygen-free atmosphere provided by delivering argon from a supply 65 to the curing chamber 60. The argon is passed through a flask 66 of de-ionized water 67 in order to humidify it. The atmosphere surrounding the tip in the pipet is oxygen-free. Elimination of oxygen is critically important, for otherwise the oxygen, which competes against the acrylamide monomers for the initiator, will slow the curing process and decrease the sensitivity of the sensor.

The HOPSA-derivative/hydrogel sensor matrix was prepared by first preparing and combining a sensor solution and an initiator solution. The sensor solution was prepared by completely dissolving (for five to ten minutes) the following dry reagents in 0.006 L of Tris(-hydroxymethyl)aminomethane buffer (pH=8.75 @ 25°C.; available from Polysciences, Inc.):

1.8750 g Acrylamide (ultra pure);
0.0625 g N,N'-Methylene-bis-acrylamide (ultra pure); and
0.009 g di-substituted HOPSA (2-propenyl) sulfonamido
(prepared by Battelle, Columbus Div.)

The preferred concentration of the di-substituted HOPSA in the hydrogel solution, found to give the best combination of stability and high sensitivity of the resulting sensor gel, was 1.5 mg of di-substituted HOPSA per 1.0 mL of hydrogel solution.

Once the above reagents were completely dissolved in the buffer, the solution was filtered through a filter having a 0.45 micron pore size to remove any contaminants, e.g., dust. Following filtration, the solution was purged with argon (industrial grade) for approximately five minutes to expel any oxygen from the solution.

The initiator solution was prepared by dissolving 0.32 g of VA-044 in 0.01 L of distilled water. VA-044 is the trade name of Wako Pure Chemical Industries, Ltd. for their Azo-polymerization initiator 2,2'-Azobis(N,N'-dimethyleneisobutyramidine) dihydrochloride, which has a molecular weight of 323.33. While VA-044 is the preferred polymerization initiator, V-50 may also be used. V-50 is the trade name of Wako Pure Chemical Industries, Ltd. for the initiator 2,2'-Azobis(2-amidinopropane) dihydrochloride, which has a molecular weight of 271.27.

Subsequently, the di-substituted HOPSA/acrylamide hydrogel sensor matrix was prepared by adding 100 uL of the initiator solution to the sensor solution, which was placed in a Kimble 25 mL EPA vial with an open top closure and polytetra-fluoroethylene-faced silicone rubber septum. This mixture was then purged with argon for approximately five minutes to dispel any oxygen present. Sealed in this manner, the sensor-initiator solution can be stored in a freezer for extended periods of time with no ill effects.

The sensor gel was then prepared by curing the sensor matrix as described hereinabove.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. The method of making an optical fiber probe having a gel-bound dye at one end, comprising the steps of:
    sliding a sleeve over said fiber until said sleeve and fiber have aligned outer ends,
    contacting said fiber outer and with uncured gel and dye,
    withdrawing said fiber inwardly with respect to said sleeve to draw said dye into a receptacle defined by the inner wall of said sleeve and the end of said fiber,
    and curing said fiber.

2. The method as in claim 1 in which said curing step includes subjecting said gel to ultraviolet light for a limited period of time.

3. The method as in claim 1 in which said curing step is conducted in an oxygen-free atmosphere.

4. The method as in claim 1 in which said curing step is conducted in an argon atmosphere.

5. The method as in claim 4 in which said argon is moisturized.

* * * * *

UNITED STATES PATENT AND TRADEMARK OFFICE
CERTIFICATE OF CORRECTION

PATENT NO. : 5,132,057
DATED : July 21, 1992
INVENTOR(S) : Dennis M. Tomisaka et al It is certified that error appears in the above-indentified patent and that said Letters Patent is hereby corrected as shown below:

Column 4, line 53, "outer and" should read

--outer end--.

Signed and Sealed this

Twelfth Day of September, 1995

Attest:

BRUCE LEHMAN

*Attesting Officer*    *Commissioner of Patents and Trademarks*